United States Patent [19]

Tsuji et al.

[11] Patent Number: 4,810,816

[45] Date of Patent: Mar. 7, 1989

[54] PROCESS FOR THE PRODUCTION OF N-FORMYL-ASPARTYL-PHENYLALANINE OR ITS METHYL ESTER

[75] Inventors: Toshiaki Tsuji; Shinichi Kishimoto, both of Yokkaichi, Japan

[73] Assignee: Ajinomoto Co., Inc., Tokyo, Japan

[21] Appl. No.: 99,733

[22] Filed: Sep. 22, 1987

[51] Int. Cl.$^4$ .......................................... C07C 101/02
[52] U.S. Cl. ...................................... 560/41; 562/450; 260/546
[58] Field of Search ................. 560/41; 562/450, 571; 260/546

[56] References Cited

U.S. PATENT DOCUMENTS 3,933,781  1/1976  Bachman et al. ..................... 560/41

FOREIGN PATENT DOCUMENTS 2040473  4/1970  France .

OTHER PUBLICATIONS

McOmie, *Protective Groups in Organic Chemistry*, Plenum Press, London, pp. 46–49, 82–87(1973).

*Primary Examiner*—Bruce D. Gray
*Attorney, Agent, or Firm*—Oblon, Fisher, Spivak, McClelland & Maier

[57] ABSTRACT

A process for producing N-formyl-aspartylphenylalanine or its methyl ester, wherein aspartic acid is reacted with formic acid and acetic anhydride in approximately stoichiometric quantities in the presence or absence of a catalyst and phenylalanine or its methyl ester is directly added to the dehydration mixture. This process has a higher yield of the desired N-formyl-dipeptide and minimizes the amount of by-products and unreacted starting materials.

2 Claims, No Drawings

PROCESS FOR THE PRODUCTION OF N-FORMYL-ASPARTYL-PHENYLALANINE OR ITS METHYL ESTER

BACKGROUND OF THE INVENTION

1. Field of the Invention

The present invention relates to a process for the production of N-formyl-L-α-aspartyl-L-phenylalanine or its methyl ester, which is useful as an intermediate for the preparation of a dipeptide sweetener, N-α-aspartyl-L-phenylalanine methyl ester. More particularly, it relates to a process for the production of said intermediate, which comprises reacting aspartic acid with approximately stoichiometric quantities of formic acid and acetic anhydride in the presence of or in the absence of a catalyst, such as a metal oxide, a metal hydroxide or a salt thereof, to form N-formyl-aspartic anhydride, and then directly adding to the resulting reaction mixture phenylalanine or its methyl ester, so as to allow the two compounds to condense.

2. Description of the Related Art

L-α-aspartyl-L-phenylalanine methyl ester is known to be a low caloric sweetener with a strong taste very similar to that of sucrose.

In the hitherto known processes, the dipeptide ester has been prepared, for example, by reacting an N-protected-L-aspartic anhydride with an L-phenylalanine methyl ester in a solvent, followed by the elimination of the protective group (see U.S. Pat. No. 3,786,039); or by reacting an N-protected-L-aspartic anhydride with L-phenylalanine and then eliminating the protective group to give L-α-aspartyl-L-phenylalanine, followed by esterification (see Japanese Patent Publication No. 26,133/80 and U.S. Pat. No. 3,933,781). It is preferable, from an economic point of view, to use a formyl group for the protection of the amino group in any of the above processes. In cases where N-formyl-L-aspartyl anhydride is allowed to condense with L-phenylalanine or its methyl ester to obtain L-α-aspartyl-L-phenylalanine methyl ester, usually N-formyl-L-L-aspartic anhydride purified from a dehydration reaction medium must be used, resulting in practical problems. N-formyl-L-aspartic anhydride is usually produced by adding L-aspartic acid to a large excess of formic acid and acetic anhydride. In this case, a large quantity of formic acid remains in the reaction mixture even after the completion of the reaction. The formic acid not only impedes the condensation of the N-formyl-L-aspartic anhydride but also decreases the ratio of the desired N-formyl-L-α-aspartyl-L-phenylalanine (α-isomer) or its methyl ester to N-formyl-L-β-aspartyl-L-phenylalanine (β-isomer) or its methyl ester. Because of this, the N-formyl-L-aspartic anhydride must be separated from the reaction medium containing the residual formic acid, for example, by adding aromatic hydrocarbons and/or halogenated hydrocarbons to the reaction (dehydration) mixture to precipitate crystals of the anhydride (see Japanese Patent Application Laid-Open No. 91,210/76) or by allowing the reaction mixture to evaporate to dryness (see U.S. Pat. No. 3,933,781). It would be obvious to those skilled in the art that the same effect can be attained by continuous or all at once addition of a large quantity of acetic acid or aromatic hydrocarbons to the reaction mixture and then evaporating off the residual formic acid.

From an industrial viewpoint, the known processes are disadvantageous in that a large quantity of energy is required for cooling, separation or evaporation and such processes become complicated with respect to plant investment.

In addition to complication of the main processes, there is also the disadvantage that a fractionating plant must be constructed and operated for the recovery and reuse of each component from the mixture with formic acid and acetic acid or the mixture with formic acid, acetic acid and aromatic hydrocarbons, separated out of the reaction medium.

A process for producing N-formyl-L-aspartic anhydride has also been proposed in which formic acid and acetic acid are used in stoichiometric quantities with respect to L-aspartic acid (see Japanese Patent Application Laid-Open No. 46,279/84). However, this process also has a problem when applied to the synthesis of N-formyl-L-α-aspartyl-L-phenylalanine or its methyl ester (N-formyl-α-dipeptide) involving condensation with L-phenylalanine or its methyl ester. To be more specific, a long period of time (up to a hundred hours or more) is required for the dehydration, and the yield of N-formyl-L-aspartic anhydride based on the starting material, i.e., L-aspartic acid, is lower than in the process utilizing an excess of formic acid. Consequently, the process results in an increase in the amount of impurities, including unreacted starting materials, and requires separation of the crystals of the anhydride. It is therefore apparent that this process does not overcome the disadvantage in the process utilizing an excess of formic acid. In addition, this process is also disadvantageous in that the loss of the anhydride during the process of crystallization causes an apparent decrease in the yield of the N-formyl-α-dipeptide in the condensation step, calculated on the basis of the starting L-aspartic acid.

As other known processes for producing N-formyl-L-aspartic anhydride, there is one in which a fine powder of L-aspartic acid is employed (see Japanese Patent Application No. 258,765/84), and one wherein irradiation with ultrasonic waves during dehydration is employed (see Japanese Patent Application Laid-Open No. 137,875/86). It is known that in these processes the dehydration can be completed within a short period of time even when formic acid and acetic anhydride are used in small quantities. However, these processes merely make it possible to shorten the reaction time by means of the addition of such equipment as a pulverizer. In other words, the prior processes for producing N-formyl-L-aspartic anhydride merely intended to produce the anhydride in high purity and in high yield, and no considerations have been paid to its use in the following step to produce the N-formyl-α-dipeptide. Accordingly, the hitherto known processes were not satisfactory for the purpose of the present invention.

Therefore, a need continues to exist for a new process for production of N-formyl-L-α-aspartyl-L-phenylalanine or its methyl ester.

SUMMARY OF THE INVENTION

Accordingly, it is an object of the present invention to provide a process for production of N-formyl-L-α-aspartyl-L-phenylalanine or its methyl ester, which is useful as an intermediate for the preparation of the dipeptide sweetener, N-α-aspartyl-L-phenylalanine methyl ester.

According to the present invention, the foregoing and other objects which will hereinafter become more readily apparent are attained by the discovery that N-formyl-L-α-phenylalanine or its methyl ester can be produced in high yield by directly adding phenylalanine or its methyl ester to a reaction mixture obtained by reacting aspartic acid with stoichiometric quantities of formic acid and acetic anhydride in the presence or absence of a catalyst. The present invention, which makes it possible to reduce the number of steps and can be highly advantageous in industrial production, has been completed on the basis of the above finding.

DETAILED DESCRIPTION OF THE PREFERRED EMBODIMENTS

A characteristic feature of the present invention is that the crystals of N-formyl-aspartic anhydride are obtained at the end of the first step (dehydration of aspartic acid) in the state of a suspension in acetic acid, which is free from residual formic acid and acetic anhydride. The process of the present invention has the advantage that the reaction mixture from the first step can be used as it is for the condensation in the second step, without such steps as crystallization, separation, evaporation, etc. and with no loss of N-formyl-aspartic anhydride formed. In addition, the process of the present invention is also quite advantageous in that the formation of the β-isomer (N-formyl-β-dipeptide) can be suppressed and the yield of the α-isomer can be markedly increased when the condensation is carried out in acetic acid or in a reaction medium containing acetic acid (see Japanese Patent Application Laid-Open No. 113,841/76 and U.S. Pat. No. 3,933,781, which is hereby incorporated by reference). In the prior dehydration process for producing N-formyl-L-aspartic anhydride, the acetic acid contained in the reaction mixture must be once removed, and next, acetic acid must be added again to the anhydride obtained. The process of the present invention is free from such inefficient additional steps.

In the process of the present invention, the L-isomer of aspartic acid is used since the object of the present invention is to produce the L,L-isomer of the N-formyl-α-dipeptide. However, it may contain its D-isomer in an amount not causing adverse effects in the following steps.

In the process of the present invention, formic acid and acetic anhydride must be used in stoichiometric quantities with respect to aspartic acid. To be more specific, it is most preferable to use one mole of formic acid and 2 moles of acetic anhydride, per mole of aspartic acid. However, good results can be obtained by using from 0.9 to 1.1 moles of formic acid and from 1.9 to 2.1 moles of acetic anhydride, respectively, per mole of aspartic acid. If the amount of formic acid used in the reaction is insufficient, the formylation step for protecting the amino group of the aspartic acid proceeds only at a low rate, and when it is used excessively, the condensation in the second step proceeds only at an insufficient rate. Similarly, when acetic anhydride is used in an insufficient amount, the yield of the dehydrated product will become lower, and the overall yield of the desired product will become lower when it is used in an excessive amount. In order to maximize the overall yield of the N-formyl-α-dipeptide from the starting material, i.e., aspartic acid, the raw materials must be used in stoichiometric quantities within the range described hereinabove.

Examples of metal compounds which may be used as a catalyst for the dehydration reaction include oxides and hydroxides of a variety of metals, including alkali metals, such as lithium, sodium, calcium, etc., alkaline earth metals, such as magnesium, calcium, etc., elements of the copper group, such as copper, etc., elements of the zinc group, such as zinc, etc., elements of the boron group, such as aluminum, etc., and elements of the iron group, such as iron, etc., as well as as their salts with various acids, for example, carbonates, carboxylic salts (e.g., salts with acetic acid), hydrochloric salts (hydrochlorides), hydrobromic salts (hydrobromides), nitrates, phosphates, sulfates and the like (see Japanese Patent Application Laid-Open No. 175,484/84).

Although there are no particular limitations on the amount of catalysts to be used, they are usually used in an amount not causing adverse effects in the following steps. The amount of catalysts to be used depends on the kind of catalysts used. Good results can be obtained by the use of even an extremely small amount of catalyst, as shown, for example, in Example 1, wherein 0.001 moles of magnesium acetate is used per mole of L-aspartic acid. The amount of catalyst to be used when the process of the invention is practiced on a commercial scale can be determined without difficulty by those skilled in the art by means of preliminary experiments. They are usually added before the start of the dehydration; however, it is also possible to add the catalyst to the reaction medium during the course of the reaction. In the process of the invention, the use of catalysts is almost indispensable to minimize the amount of by-products formed and the amount of the starting materials that remain unreacted. However, there is no need to use catalysts in cases where the formation of by-products and the presence of unreacted starting materials are permissible.

The dehydration is preferably carried out at a temperature not higher than 100° C., but not lower than 10° C. It is most preferable to carry out the reaction at a temperature of from 45° C. to 65° C. in order to prevent the racemization of the reaction product and to shorten the reaction time.

In the second step of the process of the invention, the L-isomer of phenylalanine or its methyl ester is used, however, D-isomers may be contained therein in an amount not causing adverse effects in the following steps. Phenylalanine and its methyl ester to be added to the reaction dehydration mixture can be either in the form of crystals or in the form of a solution or a suspension in an appropriate non-aqueous medium, such as acetic acid, toluene, and the like.

There are no particular limitations on the reaction temperature of the condensation. There is no need of heating since the condensation proceeds within a short period of time even at room temperature. It can be in the range of from −10° C. to 60° C.

The reaction mixture containing the product of the condensation, i.e., N-formyl-L-α-aspartyl-L-phenylalanine of its methyl ester can be used as it is in the following deformylation step. Where desired, the N-formyl-dipeptide or its methyl ester can be subjected to a treatment for removing or substituting the solvents by means of recrystallization, evaporation, extraction, or the like, before being subjected to deformylation.

In the case where the product formed in the second step is an ester (i.e., N-formyl-L-α-aspartyl-L-phenylalanine methyl ester), the desired final product, L-α-aspartyl-L-phenylalanine methyl ester, can be readily obtained by subjecting the ester to any of the known deformylation processes (see, e.g., Japanese Patent Application Laid-Open No. 185,545/83).

In the case where the product of the second step is a dipeptide having a free carboxyl group (i.e., N-formyl-L-α-aspartyl-L-phenylalanine), it can be deformylated and then esterified. It is also possible to effect both deformylation and esterification of the product at the same time (see U.S. Pat. No. 4,173,562 which is hereby incorporated by reference).

The invention now being generally described, the same will be better understood by reference to certain specific examples which are included herein for purposes of illustration only and are not intended to be limiting of the invention or any embodiment thereof, unless specified.

EXAMPLE 1

To 10.35 g (0.225 mol) of formic acid was added 45.99 g (0.450 mol) of acetic anhydride. Thereafter, 48 mg (0.00023 mol) of magnesium acetate (catalyst) was added thereto with stirring, and the resulting mixture was heated to a temperature of 55° C. To this was added 30.00 g (0.225 mol) of crystals of L-aspartic acid, and the reaction was allowed to proceed for 6 hours.

After the completion of the dehydration, the reaction mixture was cooled to 30° C., and 338 ml (0.203 mol) of 0.6 mol/l solution of L-phenylalanine methyl ester in toluene was added dropwise. This condensation of N-formyl-aspartic anhydride and L-phenylalanine methyl ester was allowed to proceed for 1 hour. The resulting reaction mixture was in the state of a slurry.

The reaction products were extracted with 500 ml of water, and the aqueous solution obtained was analyzed by high pressure liquid chromotography, using a "Unizir QC" column manufactured by Gasukuro Industries Co., an analyzer of the "LC-3A" type manufactured by Shimadzu Corp., and an eluent of phosphoric buffer. The products were detected at a wavelength of 210 nm.

The yield of the desired product, N-formyl-L-α-aspartyl-L-phenylalanine methyl ester was 73.0%, based on the amount of L-aspartic acid charged. The ratio of the amount of the α-isomer formed to that of the β-isomer formed as a by-product (α/β) was 4.85.

EXAMPLE 2

The preparation of N-formyl-L-α-aspartyl-L-phenylalanine methyl ester was repeated in the same manner as in Example 1, except that the catalyst was not used.

The yield of the desired methyl ester was 53.8%, based on L-aspartic acid charged. The ratio of the α-isomer to the β-isomer formed (α/β) was 3.83.

It is to be understood from the above results that when no catalysts are used in the dehydration step, a lower yield results, and the formic acid and acetic anhydride remain unreacted in larger quantities, and as a result, the yield of the α-isomer in the condensation step also decreases.

EXAMPLE 3 AND COMPARATIVE EXAMPLE 1

The preparation of N-formyl-L-α-aspartyl-L-phenylalanine methyl ester was repeated in the same manner as in Example 1, except that the molar ratios of formic acid and acetic anhydride to L-aspartic acid were changed to 1.1 and 2.1, respectively (Example 3), or to 1.2 to 2.2, respectively (Comparative Example 1). Results obtained are shown in Table 1, together with the results of Example 1.

The yields of the dehydrated products shown in the table were determined in the following manner: The dehydrations were repeated under the same conditions as described above, and the slurries obtained were condensed under reduced pressure, so as to remove the solvents by evaporation. Methanol (100 ml) was added to the residue to dissolve it. The amounts of N-formyl-L-α-aspartyl methyl ester and N-formyl-L-β-aspartyl methyl ester were determined. It is possible to know the yield of the N-formyl-L-aspartic anhydride through the determination of the quantities of the α- and the β-methyl esters since the two esters are formed when the N-formyl-L-aspartic anhydride comes into contact with methanol.

TABLE 1

| | Conditions for Dehydration | | Yield of Dehydration (%) | Yield and Ratio of N—formyl-L-α-aspartyl-phenylalanine Methyl Ester | | |
|---|---|---|---|---|---|---|
| | F.A.*¹/L-Asp (by mol) | A.A.*²/L-Asp (by mol) | | Yield (%) Based on L-Asp Charged | Yield (%) Based on Phenylalanine Methyl Ester | α/β Ratio |
| Example 1 | 1.0 | 2.0 | 90.7 | 73.0 | 80.8 | 4.85 |
| Example 3 | 1.1 | 2.1 | 96.9 | 69.0 | 76.4 | 4.81 |
| Comparative Example 1 | 1.2 | 2.2 | 97.1 | 60.0 | 66.5 | 4.80 |

[Notes]
*¹: Formic acid.
*²: Acetic anhydride.

It is to be understood from the above results that in the case where the molar ratios of formic acid and acetic anhydride to aspartic acid are greater than 1.1 and 2.1, respectively, the yield of N-formyl-L-α-aspartyl-L-phenylalanine methyl ester in the condensation step is lowered considerably.

It is also to be understood that in the case where formic acid and acetic acid are used in strictly stoichiometric quantities (Example 1), the highest yield can be attained in the condensation step even if the yield attainable in the dehydration step is more or less lower.

When the reaction mixture of the dehydration in Example 3 was cooled to 5° C. and the crystals of N-formyl-aspartic acid were collected by filtration, there was obtained a yield of 83% ([Yield in reaction]×[Yield in crystallization]). It is a matter of course that, when the same operation is applied to Example 1, the yield of the anhydride will become lower because of the loss upon crystallization. The present invention makes it possible to simplify the steps to a considerable extent in comparison with the prior processes involving the separation of the crystals of dehydrated products, and yet to attain a yield as high as in the prior processes.

EXAMPLE 4

The dehydration step in Example 1 was repeated under the same conditions. The reaction mixture obtained was heated to a temperature of 50° C., and 33.45 g (0.203 mol) of crystals of L-phenylalanine was added dropwise over a period of 45 minutes. The reaction was allowed to proceed for an additional 30 minutes, and the contents of the thus obtained reaction mixture were analyzed.

The yield of the desired product, N-formyl-L-α-aspartyl-L-phenylalanine, was 62.0%, based on the L-aspartic acid charged. The ratio of the α- to β-isomers formed (α/β) was 2.45.

COMPARATIVE EXAMPLE 2

The dehydration process described in Japanese Patent Publication No. 26,133/80 (U.S. Pat. No. 3,933,781) was employed.

To 84.8 g (1.843 mol) of formic acid was added 44.05 g (0.479 mol) of acetic anhydride, and the resulting mixture was stirred for 45 minutes at 25° C. Thereafter, 30.0 g (0.225 mol) of crystals of L-aspartic acid was added thereto, and the reaction (dehydration) was allowed to proceed for 3.5 hours.

The temperature of the thus obtained reaction mixture was raised to 50° C., and 35.33 g (0.214 mol) of crystals of L-phenylalanine were added thereto over a period of 45 minutes. The reaction (condensation) was allowed to proceed for an additional 30 minutes.

The yield of the desired product, N-formyl-L-α-aspartyl-L-phenylalanine, was 12.1%, based on the aspartic acid charged. The ratio of the α- to β-isomers formed (α/β) was 1.83.

The above is a result of a marked decrease in the yield of condensation, due to the presence of residual formic acid used in an excessive quantity in the dehydration step.

In the prior art described in U.S. Pat. No. 3,933,781, the reaction mixture is subjected, after the dehydration, to evaporation to remove the excess formic acid. In order to remove all the remaining formic acid, all the solvents, including the acetic acid formed from acetic anhydride, had to be evaporated off to give a dried residue.

To this residue was again added 306.3 g of acetic acid, and the temperature of the resulting mixture was raised to 55° C. Thereafter, 35.33 g (0.214 mol) of crystals of L-phenylalanine was added thereto over a period of 45 minutes, and the reaction was allowed to proceed for an additional 30 minutes. The desired α-dipeptide was obtained in a yield of 64%, based on the aspartic acid charged, and the ratio of the α- to β-isomers formed (α/β) was 2.37.

It can be easily understood from the above results that the present invention makes it possible to simplify the steps and to reduce the energy consumption to a considerable extent, through the elimination of the evaporation of solvents, without decrease in the yield of the desired product.

What is claimed as new and desired to be secured by Letters Patent of the United States is:

1. A process for production of N-formyl-L-α-aspartyl-L-phenylalanine or its methyl ester, which comprises reacting aspartic acid with from 0.9 to 1.1 moles of formic acid per mole of aspartic acid and from 1.9 to 2.1 moles of acetic anhydride per mole of aspartic acid in the presence or absence of a catalyst selected from the group consisting of metal oxides, metal hydroxides and their salts, to form N-formyl-aspartic anhydride; and then adding phenylalanine or its methyl ester or salt directly to the resulting reaction mixture, so as to allow the N-formyl-aspartic anhydride to react with the phenylalanine or its methyl ester or salt without separation of the N-formyl-aspartic anhydride from the reaction mixture, to thereby form N-formyl-L-α-aspartyl-L-phenylalanine or its methyl ester.

2. A process according to claim 1, wherein said reaction of aspartic acid with formic acid and acetic anhydride to form N-formyl-aspartic anhydride is carried out at a temperature of from 45° to 65° C.

* * * * *